US012565657B2

(12) United States Patent
Thompson

(10) Patent No.: US 12,565,657 B2
(45) Date of Patent: Mar. 3, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/970,618

(22) Filed: Dec. 5, 2024

(65) Prior Publication Data

US 2025/0263726 A1      Aug. 21, 2025

Related U.S. Application Data

(62) Division of application No. 18/582,272, filed on Feb. 20, 2024.

(51) Int. Cl.
*C12N 15/113* (2010.01)
*C12N 15/86* (2006.01)

(52) U.S. Cl.
CPC .......... *C12N 15/1138* (2013.01); *C12N 15/86* (2013.01); *C12N 2310/141* (2013.01); *C12N 2750/14143* (2013.01)

(58) Field of Classification Search
CPC ............................ C12N 15/86; C12N 15/111; C12N 2310/141; C12N 2750/14141
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 * | 11/2024 | Thompson | C12N 15/86 |
| 12,195,747 B1 * | 1/2025 | Thompson | C12N 15/111 |
| 12,281,309 B1 * | 4/2025 | Thompson | C12N 15/86 |
| 2016/0304869 A1 | 10/2016 | Maclean | |
| 2024/0026377 A1 | 1/2024 | Thompson | |

FOREIGN PATENT DOCUMENTS

CA          2721333 A1    10/2009

OTHER PUBLICATIONS

Gorski, S., Vogel, J. & Doudna, J., Nat Rev Mol Cell Biol 18, 215-228 (2017) (Year: 2017).*
Van den Berg, et al., pp. 1-12, Molecular Therapy—Nucleic Acids, vol. 5, 2016 (Year: 2016).*
O'Brien et al., Frontiers in Endocrinology, vol. 9, 2018, p. 1-2 (Year: 2018).*

*Homo sapiens* 5HT4, mRNA, NCBI Reference Sequence, version Feb. 2024, 10 pages, retrieved from the internet Aug. 22, 2025 (Year: 2024).*
Lam et al. 2015. Molec. Ther. Nuc. Ac. 4:e252 (Year: 2015).*
Ying et al. 2008. Mol. Biotechnol. 38:257-268 (Year: 2008).*
Denzler R et al., Mol Cell. Nov. 3, 2016;64(3):565-579 (Year: 2016).*
Lundstrom K., Viruses. Mar. 7, 2023;15(3):698 (Year: 2023).*
Kenji and Mizukami < star-protocols.cell.com/protocols/3185 >, Dec. 15, 2023, 17 pages, accessed on Sep. 9, 20225 (Year: 2023).*
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Nature (2010. Gene Expression. Scitable. Available online at Nature.com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Tritschler et al. "Concepts and limitations for learning developmental trajectories from single cell genomics." Development 146.12 (2019): dev170506.

(Continued)

*Primary Examiner* — Ram R Shukla
*Assistant Examiner* — Shabana S Meyering
(74) *Attorney, Agent, or Firm* — Gowling WLG (Canada) LLP

(57) ABSTRACT

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor, such as serotonin receptor 5HT1a, 5HT1b, 5HT1d, 5HT1e, 5HT1f, 5HT2a, 5HT2b, 5HT2c, 5HT3, 5HT4, 5HT6, or 5HT7.

4 Claims, No Drawings

Specification includes a Sequence Listing.

(56) References Cited

OTHER PUBLICATIONS

Kondratov et al. "Direct head-to-head evaluation of recombinant adeno-associated viral vectors manufactured in human versus insect cells." Molecular Therapy 25.12 (2017): 2661-2675.
Wang et al. "Adeno-associated virus vector as a platform for gene therapy delivery". Nat Rev Drug Discov. May 2019; 18(5):358-378. (Year: 2019).
Yang et al., Journal of Neuroimmunology, vol. 178, Issues 1-2, 2006, pp. 24-29, ISSN 0165-5728 (Year: 2006).
Millan, Current Opinion in Pharma cology, vol. 11, Issue 1, 2011, pp. 11-22, ISSN 1471-4892 (Year: 2011).
Francois (Journal of Neuroscience Sep. 19, 2018, 38 (38) 8200-8210) (Year: 2018).
Zuo X et al., Hepatology, 69 (5), 2031-2047 (Year: 2019).
Volpicelli, F et al., Mol Neurobiol 56, 8617-8627 (2019) (Year: 2019).

* cited by examiner

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "A8149441US-Sequence Listing.xml" created on 2024 Feb. 12 and having a size of 110,545 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA, that will suppress serotonin receptor expression.

BACKGROUND

Bioactive molecules, including complements and factors, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor. In some embodiments of the present disclosure, the target biomolecule is a serotonin receptor such as serotonin receptor 5HT1a. In some embodiments of the present disclosure, the target biomolecule is a serotonin receptor such as serotonin receptor 5HT1b. In some embodiments of the present disclosure, the target biomolecule is a serotonin receptor such as serotonin receptor 5HT1c. In some embodiments of the present disclosure, the target biomolecule is a serotonin receptor such as serotonin receptor 5HT1d. In some embodiments of the present disclosure, the target biomolecule is a serotonin receptor such as serotonin receptor 5HT1e. In some embodiments of the present disclosure, the target biomolecule is a serotonin receptor such as serotonin receptor 5HT1f. In some embodiments of the present disclosure, the target biomolecule is a serotonin receptor such as serotonin receptor 5HT2a. In some embodiments of the present disclosure, the target biomolecule is a serotonin receptor such as serotonin receptor 5HT2b. In some embodiments of the present disclosure, the target biomolecule is a serotonin receptor such as serotonin receptor 5HT2c. In some embodiments of the present disclosure, the target biomolecule is a serotonin receptor such as serotonin receptor 5HT3. In some embodiments of the present disclosure, the target biomolecule is a serotonin receptor such as serotonin receptor 5HT4. In some embodiments of the present disclosure, the target biomolecule is a serotonin receptor such as serotonin receptor 5HT6. In some embodiments of the present disclosure, the target biomolecule is a serotonin receptor such as serotonin receptor 5HT7.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets the mRNA of serotonin receptor 5HT1a.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets the mRNA of serotonin receptor 5HT1b.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets the mRNA of serotonin receptor 5HT1d.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets the mRNA of serotonin receptor 5HT1e.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets the mRNA of serotonin receptor 5HT1f.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets the mRNA of serotonin receptor 5HT2a.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets the mRNA of serotonin receptor 5HT2b.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets the mRNA of serotonin receptor 5HT2c.

Some embodiments of the present disclosure relate to a recombinant plasmid. In some embodiments of the present disclosure, the RP comprises a nucleotide sequence of SEQ ID NO. 1 and SEQ ID NO. 10. The RP comprises a nucleotide sequence encoding one or more nucleotide sequences encoding a miRNA sequence that targets the mRNA of serotonin receptor 5HT3.

Some embodiments of the present disclosure relate to a recombinant plasmid. In some embodiments of the present disclosure, the RP comprises a nucleotide sequence of SEQ ID NO. 1 and SEQ ID NO. 11. The RP comprises a nucleotide sequence encoding one or more nucleotide sequences encoding a miRNA sequence that targets the mRNA of serotonin receptor 5HT4.

Some embodiments of the present disclosure relate to a recombinant plasmid. In some embodiments of the present disclosure, the RP comprises a nucleotide sequence of SEQ ID NO. 1 and SEQ ID NO. 12. The RP comprises a nucleotide sequence encoding one or more nucleotide sequences encoding a miRNA sequence that targets the mRNA of serotonin receptor 5HT6.

Some embodiments of the present disclosure relate to a recombinant plasmid. In some embodiments of the present disclosure, the RP comprises a nucleotide sequence of SEQ ID NO. 1 and SEQ ID NO. 13 The RP comprises a nucleotide sequence encoding one or more nucleotide sequences encoding a miRNA sequence that targets the mRNA of serotonin receptor 5HT7.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, or SEQ ID NO. 13 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence the mRNA of a target biomolecule, for example serotonin receptor 5HT1a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1d. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1d, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1e. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1e, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1f. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1f, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2c. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2c, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT3. A first approach utilizes gene vectors containing nucleotide sequences for increasing the endogenous production of one or more sequences of miRNA, which are complete or partial sequences and/or combinations thereof, that target and silence the mRNA of serotonin receptor 5HT3 which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT4 A first approach utilizes gene vectors containing nucleotide sequences for increasing the endogenous production of one or more sequences of miRNA, which are complete or partial sequences and/or combinations thereof, that target and silence the mRNA of serotonin receptor 5HT4, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT6. A first approach utilizes gene vectors containing nucleotide sequences for increasing the endogenous production of one or more sequences of miRNA, which are complete or partial sequences and/or combinations thereof, that target and silence the mRNA of serotonin receptor 5HT6, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT7. A first approach utilizes gene vectors containing nucleotide sequences for increasing the endogenous production of one or more sequences of miRNA, which are complete or partial sequences and/or combinations thereof, that target and silence the mRNA of serotonin receptor 5HT7, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more biological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a serotonin receptor that is found within a subject. A biomolecule may be endogenous or exogenous to a subject and when bioavailable the biomolecule may inhibit or stimulate a biological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is serotonin receptor 5HT1a.

In some embodiments of the present disclosure, the target biomolecule is serotonin receptor 5HT1b.

In some embodiments of the present disclosure, the target biomolecule is serotonin receptor 5HT1d.

In some embodiments of the present disclosure, the target biomolecule is serotonin receptor 5HT1e.

In some embodiments of the present disclosure, the target biomolecule is serotonin receptor 5HT1f.

In some embodiments of the present disclosure, the target biomolecule is serotonin receptor 5HT2a.

In some embodiments of the present disclosure, the target biomolecule is serotonin receptor 5HT2b.

In some embodiments of the present disclosure, the target biomolecule is serotonin receptor 5HT2c.

In some embodiments of the present disclosure, the target biomolecule is serotonin receptor 5HT3.

In some embodiments of the present disclosure, the target biomolecule is serotonin receptor 5HT4.

In some embodiments of the present disclosure, the target biomolecule is serotonin receptor 5HT6.

In some embodiments of the present disclosure, the target biomolecule is serotonin receptor 5HT7.

In some embodiments of the present disclosure, the insert comprises one or more nucleotide sequences that each encode for one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7.

In some embodiments of the present disclosure, the delivery vehicle of the RP used for gene therapy may be a vector that is comprised of a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ $TCID_{50}$/kg (50% tissue culture infective dose per kilogram of the patient's body mass). In some embodiments of the present disclosure, the therapeutically effective amount of the composition that is administered to the patient is about $1 \times 10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adeno-associated virus (AAV) genome consisting of a RP that when operable inside a target cell will cause the target cell to produce a miRNA sequence that downregulates production of a biomolecule, with examples being serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. The RP is comprised of AAV2 inverted terminal repeats (ITRs), a composite CASI promoter, a human growth hormone (HGH) signal peptide followed by a miRNA expression cassette containing up to six different miRNAs targeting the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC
```

-continued

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

-continued

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGCGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

-continued

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACC 3'

SEQ ID NO. 2 (miRNA expression cassette No. 2-serotonin receptor 5HT1a):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGATCAATCGGATTGCGGTAATCGCGTTTTGGCCTCTGACT

GACGCGATTACCGATCCGATTGATCAGGACACAAGGCCTGTTACTAGCACTCACATGGAA

CAAATGGCCTCTAGCCTGGAGGCTTGCTGAAGGCTGTATGCTGATCTTTGCTAAATTGGT

GCACGCGTTTTGGCCTCTGACTGACGCGTGCACCATTAGCAAAGATCAGGACACAAGGCC

TGTTACTAGCACTCACATGGAACAAATGGCCTCTAGCCTGGAGGCTTGCTGAAGGCTGTA

TGCTGACTTCAATCACAATTCCAGCGCCGTTTTGGCCTCTGACTGACGGCGCTGGAAGTG

ATTGAAGTCAGGACACAAGGCCTGTTACTAGCACTCACATGGAACAAATGGCCTCTCTAG

AAT 3'

SEQ ID NO. 3 (miRNA expression cassette No. 3-serotonin receptor 5HT1b):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGTAATCTTTCGCTGGCTGCAGTTCGTTTTGGCCTCTGACT

GACGAACTGCAGCGCGAAAGATTACAGGACACAAGGCCTGTTACTAGCACTCACATGGAA

CAAATGGCCTCTAGCCTGGAGGCTTGCTGAAGGCTGTATGCTGTGTTAATGCTGATGTCA

CGCTGCGTTTTGGCCTCTGACTGACGCAGCGTGACCAGCATTAACACAGGACACAAGGCC

TGTTACTAGCACTCACATGGAACAAATGGCCTCTAGCCTGGAGGCTTGCTGAAGGCTGTA

TGCTGTTCACCTGGTTAACACATACACCGTTTTGGCCTCTGACTGACGGTGTATGTGAAC

CAGGTGAACAGGACACAAGGCCTGTTACTAGCACTCACATGGAACAAATGGCCTCTCTAG

AAT 3'

SEQ ID NO. 4 (miRNA expression cassette No. 4-serotonin receptor 5HT1d):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGATTTCTTCCTGTGCGCTTTCGCCGTTTTGGCCTCTGACT

GACGGCGAAAGCGCAGGAAGAAATCAGGACACAAGGCCTGTTACTAGCACTCACATGGAA

CAAATGGCCTCTAGCCTGGAGGCTTGCTGAAGGCTGTATGCTGAGAATAATCAGATCAGC

ACGCTCGTTTTGGCCTCTGACTGACGAGCGTGCTGCTGATTATTCTCAGGACACAAGGCC

TGTTACTAGCACTCACATGGAACAAATGGCCTCTAGCCTGGAGGCTTGCTGAAGGCTGTA

TGCTGTAATCAGGCTGAATTCAGATAGCGTTTTGGCCTCTGACTGACGCTATCTGAACAG

CCTGATTACAGGACACAAGGCCTGTTACTAGCACTCACATGGAACAAATGGCCTCTCTAG

AAT 3'

SEQ ID NO. 5 (miRNA expression cassette No. 5-serotonin receptor 5HT1e):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGATAATCACCGCTGCAGGTTCAGCGTTTTGGCCTCTGACT

GACGCTGAACCTGGCGGTGATTATCAGGACACAAGGCCTGTTACTAGCACTCACATGGAA

CAAATGGCCTCTAGCCTGGAGGCTTGCTGAAGGCTGTATGCTGTTCAATCGCGTATTGGT

AATCGCGTTTTGGCCTCTGACTGACGCGATTACCAACGCGATTGAACAGGACACAAGGCC

TGTTACTAGCACTCACATGGAACAAATGGCCTCTAGCCTGGAGGCTTGCTGAAGGCTGTA

TGCTGTGATCATGCTGAAAATGGTGCACGTTTTGGCCTCTGACTGACGTGCACCATTCAG

CATGATCACAGGACACAAGGCCTGTTACTAGCACTCACATGGAACAAATGGCCTCTCTAG

AAT 3'

SEQ ID NO. 6 (miRNA expression cassette No. 6-serotonin receptor 5HT1f):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGAGGTAATATCCTGACGCTCAGCCGTTTTGGCCTCTGACT

GACGGCTGAGCGTGGATATTACCTCAGGACACAAGGCCTGTTACTAGCACTCACATGGAA

CAAATGGCCTCTAGCCTGGAGGCTTGCTGAAGGCTGTATGCTGTACAGAATCAGATAATC

AGCGCCGTTTTGGCCTCTGACTGACGGCGCTGATTCTGATTCTGTACAGGACACAAGGCC

TGTTACTAGCACTCACATGGAACAAATGGCCTCTAGCCTGGAGGCTTGCTGAAGGCTGTA

TGCTGTCATGTTTAAAAATTCGCTGCGCGTTTTGGCCTCTGACTGACGCGCAGCGAATTT

AAACATGACAGGACACAAGGCCTGTTACTAGCACTCACATGGAACAAATGGCCTCTCTAG

AAT 3'

SEQ ID NO. 7 (miRNA expression cassette No. 7-serotonin receptor 5HT2a):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGATGAATCGGGTTGTCTGAATCGCGTTTTGGCCTCTGACT

GACGCGATTCAGAACCCGATTCATCAGGACACAAGGCCTGTTACTAGCACTCACATGGAA

CAAATGGCCTCTAGCCTGGAGGCTTGCTGAAGGCTGTATGCTGAACACTTTGCTATATCA

TCCTGCGTTTTGGCCTCTGACTGACGCAGGATGATAGCAAAGTGTTCAGGACACAAGGCC

TGTTACTAGCACTCACATGGAACAAATGGCCTCTAGCCTGGAGGCTTGCTGAAGGCTGTA

TGCTGTTCTGTTCGTTAAGCTAATGCTCGTTTTGGCCTCTGACTGACGAGCATTAGCAAC

GAACAGAACAGGACACAAGGCCTGTTACTAGCACTCACATGGAACAAATGGCCTCTCTAG

AAT 3'

SEQ ID NO. 8 (miRNA expression cassette No. 8-serotonin receptor 5HT2b):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGGAGCATTAGCAATGCGAACAGAAGTTTTGGCCTCTGACT

GACTTCTGTTCGTTGCTAATGCTCCAGGACACAAGGCCTGTTACTAGCACTCACATGGAA

CAAATGGCCTCTAGCCTGGAGGCTTGCTGAAGGCTGTATGCTGAAACATAATGGATTCAG

CAGCGCGTTTTGGCCTCTGACTGACGCGCTGCTGACCATTATGTTTCAGGACACAAGGCC

TGTTACTAGCACTCACATGGAACAAATGGCCTCTAGCCTGGAGGCTTGCTGAAGGCTGTA

TGCTGTTATCTTTGCGAAGCTGCCATCCGTTTTGGCCTCTGACTGACGGATGGCAGCCGC

AAAGATAACAGGACACAAGGCCTGTTACTAGCACTCACATGGAACAAATGGCCTCTCTAG

AAT 3'

SEQ ID NO. 9 (miRNA expression cassette No. 9-serotonin receptor 5HT2c):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGGCTCCTCCACTTGGTGGTTTGGTTTTGGCCTCTGACTGA

-continued

CGCGGCAACATTCTGGTGATTACAGGACACAAGGCCTGTTACTAGCACTCACATGGAACA

AATGGCCTCTAGCCTGGAGGCTTGCTGAAGGCTGTATGCTGTCATAATCGCTATTTGGTG

CGGCGTTTTGGCCTCTGACTGACGCCGCACCAAAGCGATTATGACAGGACACAAGGCCTG

TTACTAGCACTCACATGGAACAAATGGCCTCTAGCCTGGAGGCTTGCTGAAGGCTGTATG

CTGTTCTGATCCTGAAGTTCGGGTTCGTTTTGGCCTCTGACTGACGAACCCGAACCAGGA

TCAGAACAGGACACAAGGCCTGTTACTAGCACTCACATGGAACAAATGGCCTCTCTAGAA

T 3'

SEQ ID NO. 10 (miRNA expression cassette No. 10-serotonin receptor 5HT3):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGAAATCTTCCGGTGGTTCCACTGCGTTTTGGCCTCTGACT

GACGCAGTGGAACCCGGAAGATTTCAGGACACAAGGCCTGTTACTAGCACTCACATGGAA

CAAATGGCCTCTAGCCTGGAGGCTTGCTGAAGGCTGTATGCTGATATCCTGAATATGGTA

TGCAGCGTTTTGGCCTCTGACTGACGCTGCATACCATTCAGGATATCAGGACACAAGGCC

TGTTACTAGCACTCACATGGAACAAATGGCCTCTAGCCTGGAGGCTTGCTGAAGGCTGTA

TGCTGTTTAAAGCTCAAACGCGTTCGCCGTTTTGGCCTCTGACTGACGGCGAACGCGTGA

GCTTTAAACAGGACACAAGGCCTGTTACTAGCACTCACATGGAACAAATGGCCTCTCTAG

AAT 3'

SEQ ID NO. 11 (miRNA expression cassette No. 11-serotonin receptor 5HT4):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGTAATAAAGGTCTGGGAATCACCCGTTTTGGCCTCTGACT

GACGGGTGATTCCGACCTTTATTACAGGACACAAGGCCTGTTACTAGCACTCACATGGAA

CAAATGGCCTCTAGCCTGGAGGCTTGCTGAAGGCTGTATGCTGTAATACGCCAGATCACC

ATCAGCGTTTTGGCCTCTGACTGACGCTGATGGTGCTGGCGTATTACAGGACACAAGGCC

TGTTACTAGCACTCACATGGAACAAATGGCCTCTAGCCTGGAGGCTTGCTGAAGGCTGTA

TGCTGATACAGAAACGAAGGTTCAGGCCGTTTTGGCCTCTGACTGACGGCCTGAACCCGT

TTCTGTATCAGGACACAAGGCCTGTTACTAGCACTCACATGGAACAAATGGCCTCTCTAG

AAT '

SEQ ID NO. 12 (miRNA expression cassette No. 12-serotonin receptor 5HT6):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

CTTGCTGAAGGCTGTATGCTGTCAGATCGCTGTGGTAAACAGGCGTTTTGGCCTCTGACT

GACGCCTGTTTACCAGCGATCTGACAGGACACAAGGCCTGTTACTAGCACTCACATGGAA

CAAATGGCCTCTAGCCTGGAGGCTTGCTGAAGGCTGTATGCTGAGAATCAGATCAGATAG

CGATCCGTTTTGGCCTCTGACTGACGGATCGCTATCTGCTGATTCTCAGGACACAAGGCC

TGTTACTAGCACTCACATGGAACAAATGGCCTCTAGCCTGGAGGCTTGCTGAAGGCTGTA

TGCTGAAACATGCCAACAGCAGAATGCCGTTTTGGCCTCTGACTGACGGCATTCTGCTGG

GCATGTTTCAGGACACAAGGCCTGTTACTAGCACTCACATGGAACAAATGGCCTCTCTAG

AAT 3'

SEQ ID NO. 13 (miRNA expression cassette No. 13-serotonin receptor 5HT7):
5' GCCACCATGGCCACCGGCTCTCGCACAAGCCTGCTGCTGGCTTTCGGACTGCTGTGC

CTGCCTTGGCTCCAGGAGGGCTCCGCCGCTAGCATCGATACCGTCGCTATGTGCTGGAGG

-continued

```
CTTGCTGAAGGCTGTATGCTGACAATCAGATATGGTTGCTCGGCGTTTTGGCCTCTGACT

GACGCCGAGCAACTATCTGATTGTCAGGACACAAGGCCTGTTACTAGCACTCACATGGAA

CAAATGGCCTCTAGCCTGGAGGCTTGCTGAAGGCTGTATGCTGTTTCACAATGCATCGTT

CAGCGCGTTTTGGCCTCTGACTGACGCGCTGAACGGCATTGTGAAACAGGACACAAGGCC

TGTTACTAGCACTCACATGGAACAAATGGCCTCTAGCCTGGAGGCTTGCTGAAGGCTGTA

TGCTGACAATAATGCCAACAGGGTGGTCGTTTTGGCCTCTGACTGACGACCACCCTGGGC

ATTATTGTCAGGACACAAGGCCTGTTACTAGCACTCACATGGAACAAATGGCCTCTCTAG

AAT 3'
```

SEQ ID NO. 14 = SEQ ID NO. 1 + SEQ ID NO. 2
5' AATCAACCTCTGGATTACAAAATTTGTGAAAGATTGACTGGTATTCTTAACTATGTT

```
GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT
```

-continued

```
AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT
```

-continued

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGCGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

ATCAATCGGATTGCGGTAATCGCGTTTTGGCCTCTGACTGACGCGATTACCGATCCGATT

GATCAGGACACAAGGCCTGTTACTAGCACTCACATGGAACAAATGGCCTCTAGCCTGGAG

GCTTGCTGAAGGCTGTATGCTGATCTTTGCTAAATTGGTGCACGCGTTTTGGCCTCTGAC

TGACGCGTGCACCATTAGCAAAGATCAGGACACAAGGCCTGTTACTAGCACTCACATGGA

ACAAATGGCCTCTAGCCTGGAGGCTTGCTGAAGGCTGTATGCTGACTTCAATCACAATTC

CAGCGCCGTTTTGGCCTCTGACTGACGGCGCTGGAAGTGATTGAAGTCAGGACACAAGGC

CTGTTACTAGCACTCACATGGAACAAATGGCCTCTCTAGAAT 3'

SEQ ID NO. 15 = SEQ ID NO. 1 + SEQ ID NO. 3
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

27

28

-continued

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

-continued

```
GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGCGGGGCGAGGGGCGGGGCGGGGC
```

-continued

```
GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

TAATCTTTCGCTGGCTGCAGTTCGTTTTGGCCTCTGACTGACGAACTGCAGCGCGAAAGA

TTACAGGACACAAGGCCTGTTACTAGCACTCACATGGAACAAATGGCCTCTAGCCTGGAG

GCTTGCTGAAGGCTGTATGCTGTGTTAATGCTGATGTCACGCTGCGTTTTGGCCTCTGAC

TGACGCAGCGTGACCAGCATTAACACAGGACACAAGGCCTGTTACTAGCACTCACATGGA

ACAAATGGCCTCTAGCCTGGAGGCTTGCTGAAGGCTGTATGCTGTTCACCTGGTTAACAC

ATACACCGTTTTGGCCTCTGACTGACGGTGTATGTGAACCAGGTGAACAGGACACAAGGC

CTGTTACTAGCACTCACATGGAACAAATGGCCTCTCTAGAAT 3'

SEQ ID NO. 16 = SEQ ID NO. 1 + SEQ ID NO. 4
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC
```

-continued

```
CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC
```

-continued

```
TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGGGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

ATTTCTTCCTGTGCGCTTTCGCCGTTTTGGCCTCTGACTGACGGCGAAAGCGCAGGAAGA

AATCAGGACACAAGGCCTGTTACTAGCACTCACATGGAACAAATGGCCTCTAGCCTGGAG

GCTTGCTGAAGGCTGTATGCTGAGAATAATCAGATCAGCACGCTCGTTTTGGCCTCTGAC
```

-continued

TGACGAGCGTGCTGCTGATTATTCTCAGGACACAAGGCCTGTTACTAGCACTCACATGGA

ACAAATGGCCTCTAGCCTGGAGGCTTGCTGAAGGCTGTATGCTGTAATCAGGCTGAATTC

AGATAGCGTTTTGGCCTCTGACTGACGCTATCTGAACAGCCTGATTACAGGACACAAGGC

CTGTTACTAGCACTCACATGGAACAAATGGCCTCTCTAGAAT 3'

SEQ ID NO. 17 = SEQ ID NO. 1 + SEQ ID NO. 5
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

-continued

```
GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC
```

-continued

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGGGGGGGGGGCGAGGGGCGGGGCGGGGCG

AGGCGGAGAGGTGCGGCGGCAGCCAATCAGAGCGGCGCGCTCCGAAAGTTTCCTTTTATG

GCGAGGCGGCGGCGGCGGCGGCCCTATAAAAAGCGAAGCGCGCGGCGGGCGGGAGTCGCT

GCGCGCTGCCTTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTTTGGCGCCTCC

CGCGGGCGCCCCCCTCCTCACGGCGAGCGCTGCCACGTCAGACGAAGGGCGCAGCGAGCG

TCCTGATCCTTCCGCCCGGACGCTCAGGACAGCGGCCCGCTGCTCATAAGACTCGGCCTT

AGAACCCCAGTATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCATGTTCATGTTT

TCTTTTTTTTTCTACAGGTCCTGGGTGACGAACAGGGTACCGCCACCATGGCCACCGGCT

CTCGCACAAGCCTGCTGCTGGCTTTCGGACTGCTGTGCCTGCCTTGGCTCCAGGAGGGCT

CCGCCGCTAGCATCGATACCGTCGCTATGTGCTGGAGGCTTGCTGAAGGCTGTATGCTGA

TAATCACCGCTGCAGGTTCAGCGTTTTGGCCTCTGACTGACGCTGAACCTGGCGGTGATT

ATCAGGACACAAGGCCTGTTACTAGCACTCACATGGAACAAATGGCCTCTAGCCTGGAGG

CTTGCTGAAGGCTGTATGCTGTTCAATCGCGTATTGGTAATCGCGTTTTGGCCTCTGACT

GACGCGATTACCAACGCGATTGAACAGGACACAAGGCCTGTTACTAGCACTCACATGGAA

CAAATGGCCTCTAGCCTGGAGGCTTGCTGAAGGCTGTATGCTGTGATCATGCTGAAAATG

GTGCACGTTTTGGCCTCTGACTGACGTGCACCATTCAGCATGATCACAGGACACAAGGCC

TGTTACTAGCACTCACATGGAACAAATGGCCTCTCTAGAAT 3'

SEQ ID NO. 18 = SEQ ID NO. 1 + SEQ ID NO. 6
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

-continued

```
TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT
```

-continued

```
GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGGGGGCGGGGCGAGGGGGGGGCGGGGCGA

GGCGGAGAGGTGCGGCGGCAGCCAATCAGAGCGGCGCGCTCCGAAAGTTTCCTTTTATGG

CGAGGCGGCGGCGGCGGCGGCCCTATAAAAAGCGAAGCGCGCGGCGGGCGGGAGTCGCTG

CGCGCTGCCTTCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTTGGCGCCTCCC

GCGGGCGCCCCCCTCCTCACGGCGAGCGCTGCCACGTCAGACGAAGGGCGCAGCGAGCGT
```

CCTGATCCTTCCGCCCGGACGCTCAGGACAGCGGCCCGCTGCTCATAAGACTCGGCCTTA

GAACCCCAGTATCAGCAGAAGGACATTTTAGGACGGGACTTGGGTGACTCTAGGGCACTG

GTTTTCTTTCCAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATGTTCATGTTTT

CTTTTTTTTTCTACAGGTCCTGGGTGACGAACAGGGTACCGCCACCATGGCCACCGGCTC

TCGCACAAGCCTGCTGCTGGCTTTCGGACTGCTGTGCCTGCCTTGGCTCCAGGAGGGCTC

CGCCGCTAGCATCGATACCGTCGCTATGTGCTGGAGGCTTGCTGAAGGCTGTATGCTGAG

GTAATATCCTGACGCTCAGCCGTTTTGGCCTCTGACTGACGGCTGAGCGTGGATATTACC

TCAGGACACAAGGCCTGTTACTAGCACTCACATGGAACAAATGGCCTCTAGCCTGGAGGC

TTGCTGAAGGCTGTATGCTGTACAGAATCAGATAATCAGCGCCGTTTTGGCCTCTGACTG

ACGGCGCTGATTCTGATTCTGTACAGGACACAAGGCCTGTTACTAGCACTCACATGGAAC

AAATGGCCTCTAGCCTGGAGGCTTGCTGAAGGCTGTATGCTGTCATGTTTAAAAATTCGC

TGCGCGTTTTGGCCTCTGACTGACGCGCAGCGAATTTAAACATGACAGGACACAAGGCCT

GTTACTAGCACTCACATGGAACAAATGGCCTCTCTAGAAT 3'

SEQ ID NO. 19 = SEQ ID NO. 1 + SEQ ID NO. 7
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

-continued

```
GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG
```

-continued

```
CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGGGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

ATGAATCGGGTTGTCTGAATCGCGTTTTGGCCTCTGACTGACGCGATTCAGAACCCGATT

CATCAGGACACAAGGCCTGTTACTAGCACTCACATGGAACAAATGGCCTCTAGCCTGGAG

GCTTGCTGAAGGCTGTATGCTGAACACTTTGCTATATCATCCTGCGTTTTGGCCTCTGAC

TGACGCAGGATGATAGCAAAGTGTTCAGGACACAAGGCCTGTTACTAGCACTCACATGGA

ACAAATGGCCTCTAGCCTGGAGGCTTGCTGAAGGCTGTATGCTGTTCTGTTCGTTAAGCT
```

-continued

AATGCTCGTTTTGGCCTCTGACTGACGAGCATTAGCAACGAACAGAACAGGACACAAGGC

CTGTTACTAGCACTCACATGGAACAAATGGCCTCTCTAGAAT 3'

SEQ ID NO. 20 = SEQ ID NO. 1 + SEQ ID NO. 8
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

-continued

```
TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG
```

-continued

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGGGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

GAGCATTAGCAATGCGAACAGAAGTTTTGGCCTCTGACTGACTTCTGTTCGTTGCTAATG

CTCCAGGACACAAGGCCTGTTACTAGCACTCACATGGAACAAATGGCCTCTAGCCTGGAG

GCTTGCTGAAGGCTGTATGCTGAAACATAATGGATTCAGCAGCGCGTTTTGGCCTCTGAC

TGACGCGCTGCTGACCATTATGTTTCAGGACACAAGGCCTGTTACTAGCACTCACATGGA

ACAAATGGCCTCTAGCCTGGAGGCTTGCTGAAGGCTGTATGCTGTTATCTTTGCGAAGCT

GCCATCCGTTTTGGCCTCTGACTGACGGATGGCAGCCGCAAAGATAACAGGACACAAGGC

CTGTTACTAGCACTCACATGGAACAAATGGCCTCTCTAGAAT 3'

SEQ ID NO. 21 = SEQ ID NO. 1 + SEQ ID NO. 9
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

-continued

```
TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTTGCACAACATGGGGGATCATGTAACTCGCCTTGATCGTTGGGAACCGGAGCT
```

-continued

```
GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGGGGGGGGGGCGAGGGGCGGGGCGGGGCG

AGGCGGAGAGGTGCGGCGGCAGCCAATCAGAGCGGCGCGCTCCGAAAGTTTCCTTTTATG

GCGAGGCGGCGGCGGCGGCGGCCCTATAAAAAGCGAAGCGCGCGGCGGGCGGGAGTCGCT

GCGCGCTGCCTTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTTTGGCGCCTCC

CGCGGGCGCCCCCCTCCTCACGGCGAGCGCTGCCACGTCAGACGAAGGGCGCAGCGAGCG

TCCTGATCCTTCCGCCCGGACGCTCAGGACAGCGGCCCGCTGCTCATAAGACTCGGCCTT

AGAACCCCAGTATCAGCAGAAGGACATTTTAGGACGGGACTTGGGTGACTCTAGGGCACT
```

-continued

GGTTTTCTTTCCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCATGTTCATGTTT

TCTTTTTTTTTCTACAGGTCCTGGGTGACGAACAGGGTACCGCCACCATGGCCACCGGCT

CTCGCACAAGCCTGCTGCTGGCTTTCGGACTGCTGTGCCTGCCTTGGCTCCAGGAGGGCT

CCGCCGCTAGCATCGATACCGTCGCTATGTGCTGGAGGCTTGCTGAAGGCTGTATGCTGG

CTCCTCCACTTGGTGGTTTGGTTTTGGCCTCTGACTGACGCGGCAACATTCTGGTGATTA

CAGGACACAAGGCCTGTTACTAGCACTCACATGGAACAAATGGCCTCTAGCCTGGAGGCT

TGCTGAAGGCTGTATGCTGTCATAATCGCTATTTGGTGCGGCGTTTTGGCCTCTGACTGA

CGCCGCACCAAAGCGATTATGACAGGACACAAGGCCTGTTACTAGCACTCACATGGAACA

AATGGCCTCTAGCCTGGAGGCTTGCTGAAGGCTGTATGCTGTTCTGATCCTGAAGTTCGG

GTTCGTTTTGGCCTCTGACTGACGAACCCGAACCAGGATCAGAACAGGACACAAGGCCTG

TTACTAGCACTCACATGGAACAAATGGCCTCTCTAGAAT 3'

SEQ ID NO. 22 = SEQ ID NO. 1 + SEQ ID NO. 10
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

65

66

```
GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA
```

-continued

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGCGCGCGCCAGGCGGGGCGGGGCGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

AAATCTTCCGGTGGTTCCACTGCGTTTTGGCCTCTGACTGACGCAGTGGAACCCGGAAGA

TTTCAGGACACAAGGCCTGTTACTAGCACTCACATGGAACAAATGGCCTCTAGCCTGGAG

GCTTGCTGAAGGCTGTATGCTGATATCCTGAATATGGTATGCAGCGTTTTGGCCTCTGAC

TGACGCTGCATACCATTCAGGATATCAGGACACAAGGCCTGTTACTAGCACTCACATGGA

ACAAATGGCCTCTAGCCTGGAGGCTTGCTGAAGGCTGTATGCTGTTTAAAGCTCAAACGC

GTTCGCCGTTTTGGCCTCTGACTGACGGCGAACGCGTGAGCTTTAAACAGGACACAAGGC

CTGTTACTAGCACTCACATGGAACAAATGGCCTCTCTAGAAT 3'

SEQ ID NO. 23 = SEQ ID NO:. 1 + SEQ ID NO. 11
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

-continued

```
CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG
```

-continued

```
AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT
```

-continued

```
ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGGCGCGCGCCAGGCGGGGCGGGGGGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

TAATAAAGGTCTGGGAATCACCCGTTTTGGCCTCTGACTGACGGGTGATTCCGACCTTTA

TTACAGGACACAAGGCCTGTTACTAGCACTCACATGGAACAAATGGCCTCTAGCCTGGAG

GCTTGCTGAAGGCTGTATGCTGTAATACGCCAGATCACCATCAGCGTTTTGGCCTCTGAC

TGACGCTGATGGTGCTGGCGTATTACAGGACACAAGGCCTGTTACTAGCACTCACATGGA

ACAAATGGCCTCTAGCCTGGAGGCTTGCTGAAGGCTGTATGCTGATACAGAAACGAAGGT

TCAGGCCGTTTTGGCCTCTGACTGACGGCCTGAACCCGTTTCTGTATCAGGACACAAGGC

CTGTTACTAGCACTCACATGGAACAAATGGCCTCTCTAGAAT 3'
```

SEQ ID NO. 24 = SEQ ID NO. 1 + SEQ ID NO. 12

```
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT
```

-continued

```
TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC
```

```
TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC

TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

GGGGGGGGGGGGGGCGCGCGCCAGGCGGGGCGGGGCGGGGCGAGGGGCGGGGCGGGGCG

AGGCGGAGAGGTGCGGCGGCAGCCAATCAGAGCGGCGCGCTCCGAAAGTTTCCTTTTATG

GCGAGGCGGCGGCGGCGGCGGCCCTATAAAAAGCGAAGCGCGCGGCGGGCGGGAGTCGCT

GCGCGCTGCCTTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTTTGGCGCCTCC

CGCGGGCGCCCCCCTCCTCACGGCGAGCGCTGCCACGTCAGACGAAGGGCGCAGCGAGCG

TCCTGATCCTTCCGCCCGGACGCTCAGGACAGCGGCCCGCTGCTCATAAGACTCGGCCTT

AGAACCCCAGTATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCATGTTCATGTTT

TCTTTTTTTTTTCTACAGGTCCTGGGTGACGAACAGGGTACCGCCACCATGGCCACCGGCT

CTCGCACAAGCCTGCTGCTGGCTTTCGGACTGCTGTGCCTGCCTTGGCTCCAGGAGGGCT
```

-continued

CCGCCGCTAGCATCGATACCGTCGCTATGTGCTGGAGGCTTGCTGAAGGCTGTATGCTGT

CAGATCGCTGTGGTAAACAGGCGTTTTGGCCTCTGACTGACGCCTGTTTACCAGCGATCT

GACAGGACACAAGGCCTGTTACTAGCACTCACATGGAACAAATGGCCTCTAGCCTGGAGG

CTTGCTGAAGGCTGTATGCTGAGAATCAGATCAGATAGCGATCCGTTTTGGCCTCTGACT

GACGGATCGCTATCTGCTGATTCTCAGGACACAAGGCCTGTTACTAGCACTCACATGGAA

CAAATGGCCTCTAGCCTGGAGGCTTGCTGAAGGCTGTATGCTGAAACATGCCAACAGCAG

AATGCCGTTTTGGCCTCTGACTGACGGCATTCTGCTGGGCATGTTTCAGGACACAAGGCC

TGTTACTAGCACTCACATGGAACAAATGGCCTCTCTAGAAT 3'

SEQ ID NO. 25 = SEQ ID NO. 1 + SEQ ID NO. 13
5' AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGACGCAACCCCC

ACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGG

CTGTTGGGCACTGACAATTCCGTGGTGTTGTCGGGGAAATCATCGTCCTTTCCTTGGCTG

CTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGT

CTTCGCCTTCGCCCTCAGACGAGTCGGATCTCCCTTTGGGCCGCCTCCCCGCCTAAGCTT

ATCGATACCGTCGAGATCTAACTTGTTTATTGCAGCTTATAATGGTTACAAATAAAGCAA

TAGCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCTACG

TAGATAAGTAGCATGGCGGGTTAATCATTAACTACAAGGAACCCCTAGTGATGGAGTTGG

CCACTCCCTCTCTGCGCGCTCGCTCGCTCACTGAGGCCGGGCGACCAAAGGTCGCCCGAC

GCCCGGGCTTTGCCCGGGCGGCCTCAGTGAGCGAGCGAGCGCGCAGCTGGCGTAATAGCG

AAGAGGCCCGCACCGATCGCCCTTCCCAACAGTTGCGCAGCCTGAATGGCGAATGGCGAT

TCCGTTGCAATGGCTGGCGGTAATATTGTTCTGGATATTACCAGCAAGGCCGATAGTTTG

AGTTCTTCTACTCAGGCAAGTGATGTTATTACTAATCAAAGAAGTATTGCGACAACGGTT

AATTTGCGTGATGGACAGACTCTTTTACTCGGTGGCCTCACTGATTATAAAAACACTTCT

CAGGATTCTGGCGTACCGTTCCTGTCTAAAATCCCTTTAATCGGCCTCCTGTTTAGCTCC

CGCTCTGATTCTAACGAGGAAAGCACGTTATACGTGCTCGTCAAAGCAACCATAGTACGC

GCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGC

TTTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGACT

CTTGTTCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTTAACGC

GAATTTTAACAAAATATTAACGTTTACAATTTAAATATTTGCTTATACAATCTTCCTGTT

TTTGGGGCTTTTCTGATTATCAACCGGGGTACATATGATTGACATGCTAGTTTTACGATT

ACCGTTCATCGATTCTCTTGTTTGCTCCAGACTCTCAGGCAATGACCTGATAGCCTTTGT

-continued

```
AGAGACCTCTCAAAAATAGCTACCCTCTCCGGCATGAATTTATCAGCTAGAACGGTTGAA

TATCATATTGATGGTGATTTGACTGTCTCCGGCCTTTCTCACCCGTTTGAATCTTTACCT

ACACATTACTCAGGCATTGCATTTAAAATATATGAGGGTTCTAAAAATTTTTATCCTTGC

GTTGAAATAAAGGCTTCTCCCGCAAAAGTATTACAGGGTCATAATGTTTTTGGTACAACC

GATTTAGCTTTATGCTCTGAGGCTTTATTGCTTAATTTTGCTAATTCTTTGCCTTGCCTG

TATGATTTATTGGATGTTGGAATTCCTGATGCGGTATTTTCTCCTTACGCATCTGTGCGG

TATTTCACACCGCATATGGTGCACTCTCAGTACAATCTGCTCTGATGCCGCATAGTTAAG

CCAGCCCCGACACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGAGGTTTTCACC

GTCATCACCGAAACGCGCGAGACGAAAGGGCCTCGTGATACGCCTATTTTTATAGGTTAA

TGTCATGATAATAATGGTTTCTTAGACGTCAGGTGGCACTTTTCGGGGAAATGTGCGCGG

AACCCCTATTTGTTTATTTTTCTAAATACATTCAAATATGTATCCGCTCATGAGACAATA

ACCCTGATAAATGCTTCAATAATATTGAAAAAGGAAGAGTATGAGTATTCAACATTTCCG

TGTCGCCCTTATTCCCTTTTTTGCGGCATTTTGCCTTCCTGTTTTTGCTCACCCAGAAAC

GCTGGTGAAAGTAAAAGATGCTGAAGATCAGTTGGGTGCACGAGTGGGTTACATCGAACT

GGATCTCAACAGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCAC

AGAAAAGCATCTTACGGATGGCATGACAGTAAGAGAATTATGCAGTGCTGCCATAACCAT

GAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCT

GAATGAAGCCATACCAAACGACGAGCGTGACACCACGATGCCTGTAGCAATGGCAACAAC

GTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAAC

TATGGATGAACGAAATAGACAGATCGCTGAGATAGGTGCCTCACTGATTAAGCATTGGTA

ACTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCC

TTTTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTC

TGTAGCACCGCCTACATACCTCGCTCTGCTAATCCTGTTACCAGTGGCTGCTGCCAGTGG

CGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAGAAAGGC

GGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGCCTT

TTTACGGTTCCTGGCCTTTTGCTGGCCTTTTGCTCACATGTTCTTTCCTGCGTTATCCCC
```

-continued

```
TGATTCTGTGGATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCAATACGCAAACC

GCCTCTCCCCGCGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGGCCTCAGTGAGC

GAGCGAGCGCGCAGAGAGGGAGTGGCCAACTCCATCACTAGGGGTTCCTTGTAGTTAATG

ATTAACCCGCCATGCTACTTATCTACGTAGCCATGCTCTAGGACATTGATTATTGACTAG

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCA

TCGCTATTACCATGGTCGAGGTGAGCCCCACGTTCTGCTTCACTCTCCCCATCTCCCCCC

CCTCCCCACCCCCAATTTTGTATTTATTTATTTTTTAATTATTTTGTGCAGCGATGGGGG

CGGGGGGGGGGGGGGGCGCGCGCCAGGCGGGGCGGGGGGGGGCGAGGGGCGGGGCGGGGC

GAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGAGTCGC

TGCGCGCTGCCTTCGCCCCGTGCCCCGCTCCGCCGCCGCCTCGCGCCGCCCGCCCCGGCT

CTGACTGACCGCGTTACTAAAACAGGTAAGTCCGGCCTCCGCGCCGGGTTTTGGCGCCTC

CCGCGGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGGCCT

TAGAACCCCAGTATCAGCAGAAGGACATTTTAGGACGGGACTTGGGTGACTCTAGGGCAC

TGGTTTTCTTTCCAGAGAGCGGAACAGGCGAGGAAAAGTAGTCCCTTCTCGGCGATTCTG

CGGAGGGATCTCCGTGGGGCGGTGAACGCCGATGATGCCTCTACTAACCATGTTCATGTT

TTCTTTTTTTTCTACAGGTCCTGGGTGACGAACAGGGTACCGCCACCATGGCCACCGGC

TCTCGCACAAGCCTGCTGCTGGCTTTCGGACTGCTGTGCCTGCCTTGGCTCCAGGAGGGC

TCCGCCGCTAGCATCGATACCGTCGCTATGTGCTGGAGGCTTGCTGAAGGCTGTATGCTG

ACAATCAGATATGGTTGCTCGGCGTTTTGGCCTCTGACTGACGCCGAGCAACTATCTGAT

TGTCAGGACACAAGGCCTGTTACTAGCACTCACATGGAACAAATGGCCTCTAGCCTGGAG

GCTTGCTGAAGGCTGTATGCTGTTTCACAATGCATCGTTCAGCGCGTTTTGGCCTCTGAC

TGACGCGCTGAACGGCATTGTGAAACAGGACACAAGGCCTGTTACTAGCACTCACATGGA

ACAAATGGCCTCTAGCCTGGAGGCTTGCTGAAGGCTGTATGCTGACAATAATGCCAACAG

GGTGGTCGTTTTGGCCTCTGACTGACGACCACCCTGGGCATTATTGTCAGGACACAAGGC

CTGTTACTAGCACTCACATGGAACAAATGGCCTCTCTAGAAT 3'
```

55

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24 and SEQ ID NO. 25, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes were integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) comprising a sequence of nucleotides that is SEQ ID NO. 11.

2. The composition of claim 1, wherein the RP is encapsulated in a protein coat, a lipid vesicle, or any combination thereof.

3. A composition that comprises a recombinant plasmid (RP) comprising with a sequence of nucleotides that is SEQ ID NO. 23.

4. The composition of claim 3, wherein the RP is encapsulated in a protein coat, a lipid vesicle, or any combination thereof.

* * * * *

```
                           SEQUENCE LISTING

Sequence total quantity: 25
SEQ ID NO: 1              moltype = DNA   length = 5799
FEATURE                  Location/Qualifiers
source                   1..5799
                         mol_type = other DNA
                         organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataaccc    2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
```

-continued

```
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag acccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt    4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagc ggccaactcc atcactaggg gttccttgta gttaatgatt   4680
aacccgccat gctacttatc tacgtagcca tgctctagga cattgattat tgactagttg   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg    4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggggg   5160
gggggggggg gggcgcgcgc caggcggggc ggggcggggc gagggggcggg gcggggcgga   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttcttcc agagagcgga acaggcgagg aaaagtagtc cttctcggc gattctgcgg    5700
agggatctcc gtggggcggt gaacgccgat gatgcctcta ctaaccatgt tcatgttttc   5760
ttttttttttc tacaggtcct gggtgacgaa caggtacc                          5799
```

```
SEQ ID NO: 2                 moltype = DNA  length = 540
FEATURE                      Location/Qualifiers
source                       1..540
                             mol_type = other DNA
                             organism = synthetic construct
SEQUENCE: 2
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgat caatcggatt gcggtaactg cgtttggcc tctgactgac    180
gcgattaccg atccgattga tcaggacaca aggcctgtta ctagcactca catggaacaa   240
atggcctcta gcctggaggc ttgctgaagg ctgtatgctg atctttgcta aattggtgca   300
cgcgttttgg cctctgactg acgcgtgcac cattagcaaa gatcaggaca caaggcctgt   360
tactagcact cacatggaac aaatggcctc tagcctggag gcttgctgaa ggctgtatgc   420
tgacttcaat cacaattcca gcgccgtttt ggcctctgac tgacggcgct ggaagtgatt   480
gaagtcagga cacaaggcct gttactagca ctcacatgga acaaatggcc tctctagaat   540
```

```
SEQ ID NO: 3                 moltype = DNA  length = 540
FEATURE                      Location/Qualifiers
source                       1..540
                             mol_type = other DNA
                             organism = synthetic construct
SEQUENCE: 3
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgta atctttcgct ggctgcagtt cgtttggcc tctgactgac    180
gaactgcagc gcgaaagatt acaggacaca aggcctgtta ctagcactca catggaacaa   240
atggcctcta gcctggaggc ttgctgaagg ctgtatgctg tgttaatgct gatgtcacgc   300
tgcgttttgg cctctgactg acgcagcgtg accagcatta acacaggaca caaggcctgt   360
tactagcact cacatggaac aaatggcctc tagcctggag gcttgctgaa ggctgtatgc   420
tgttcacctg gttaacacat acaccgtttt ggcctctgac tgacggtgta tgtgaaccag   480
gtgaacagga cacaaggcct gttactagca ctcacatgga acaaatggcc tctctagaat   540
```

```
SEQ ID NO: 4                 moltype = DNA  length = 540
```

```
FEATURE              Location/Qualifiers
source               1..540
                     mol_type = other DNA
                     organism = synthetic construct
SEQUENCE: 4
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgat ttcttcctgt gcgctttcgc cgttttggcc tctgactgac  180
ggcgaaagcg caggaagaaa tcaggacaca aggcctgtta ctagcactca catggaacaa  240
atggcctcta gcctggaggc ttgctgaagg ctgtatgctg agaataatca gatcagcacg  300
ctcgttttgg cctctgactg acgagcgtgc tgctgattat tctcaggaca caaggcctgt  360
tactagcact cacatggaac aaatggcctc tagcctggag gcttgctgaa ggctgtatgc  420
tgtaatcagg ctgaattcag atagcgtttt ggcctctgac tgacgctatc tgaacagcct  480
gattacagga cacaaggcct gttactagca ctcacatgga acaaatggcc tctctagaat  540

SEQ ID NO: 5           moltype = DNA   length = 540
FEATURE                Location/Qualifiers
source                 1..540
                       mol_type = other DNA
                       organism = synthetic construct
SEQUENCE: 5
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgat aatcaccgct gcaggttcag cgttttggcc tctgactgac  180
gctgaacctg cgcgtgatta tcaggacaca aggcctgtta ctagcactca catggaacaa  240
atggcctcta gcctggaggc ttgctgaagg ctgtatgctg ttcaatcgtc tattggtaat  300
cgcgttttgg cctctgactg acgcgattac caacgcgatt gaacaggaca caaggcctgt  360
tactagcact cacatggaac aaatggcctc tagcctggag gcttgctgaa ggctgtatgc  420
tgtgatcatg ctgaaaatgg tgcacgtttt ggcctctgac tgacgtgcac cattcagcat  480
gatcacagga cacaaggcct gttactagca ctcacatgga acaaatggcc tctctagaat  540

SEQ ID NO: 6           moltype = DNA   length = 540
FEATURE                Location/Qualifiers
source                 1..540
                       mol_type = other DNA
                       organism = synthetic construct
SEQUENCE: 6
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgag gtaatatcct gacgctcagc cgttttggcc tctgactgac  180
ggctgagcgt ggatattacc tcaggacaca aggcctgtta ctagcactca catggaacaa  240
atggcctcta gcctggaggc ttgctgaagg ctgtatgctg tacagaatca gataatcagc  300
gccgttttgg cctctgactg acggcgctga ttctgattct gtacaggaca caaggcctgt  360
tactagcact cacatggaac aaatggcctc tagcctggag gcttgctgaa ggctgtatgc  420
tgtcatgttt aaaaattcgc tgcgcgtttt ggcctctgac tgacgcgcag cgaatttaaa  480
catgacagga cacaaggcct gttactagca ctcacatgga acaaatggcc tctctagaat  540

SEQ ID NO: 7           moltype = DNA   length = 540
FEATURE                Location/Qualifiers
source                 1..540
                       mol_type = other DNA
                       organism = synthetic construct
SEQUENCE: 7
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgat gaatcgggtt gtctgaatcg cgttttggcc tctgactgac  180
gcgattcaga acccgattca tcaggacaca aggcctgtta ctagcactca catggaacaa  240
atggcctcta gcctggaggc ttgctgaagg ctgtatgctg aacactttgc tatatcatcc  300
tgcgttttgg cctctgactg acgcaggatg atagcaaagt gttcaggaca caaggcctgt  360
tactagcact cacatggaac aaatggcctc tagcctggag gcttgctgaa ggctgtatgc  420
tgttctgttc gttaagctaa tgctcgtttt ggcctctgac tgacgagcat tagcaacgaa  480
cagaacagga cacaaggcct gttactagca ctcacatgga acaaatggcc tctctagaat  540

SEQ ID NO: 8           moltype = DNA   length = 540
FEATURE                Location/Qualifiers
source                 1..540
                       mol_type = other DNA
                       organism = synthetic construct
SEQUENCE: 8
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgga gcattagcaa tgcgaacaga agtttggcc tctgactgac   180
ttctgttcgt tgctaatgct ccaggacaca aggcctgtta ctagcactca catggaacaa  240
atggcctcta gcctggaggc ttgctgaagg ctgtatgctg aaacataatg gattcagcag  300
cgcgttttgg cctctgactg acgcgctgct gaccattatg tttcaggaca caaggcctgt  360
tactagcact cacatggaac aaatggcctc tagcctggag gcttgctgaa ggctgtatgc  420
tgttatcttt gcgaagctgc catccgtttt ggcctctgac tgacggatgg cagccgcaaa  480
gataacagga cacaaggcct gttactagca ctcacatgga acaaatggcc tctctagaat  540
```

```
SEQ ID NO: 9            moltype = DNA   length = 538
FEATURE                 Location/Qualifiers
source                  1..538
                        mol_type = other DNA
                        organism = synthetic construct
SEQUENCE: 9
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctggc tcctccactt ggtggtttgg ttttggcctc tgactgacgc  180
ggcaacattc tggtgattac aggacacaag gcctgttact agcactcaca tggaacaaat  240
ggcctctagc ctggaggctt gctgaaggct gtatgctgtc ataatcgcta tttggtgcgg  300
cgttttggcc tctgactgac gccgcaccaa agcgattatg acaggacaca aggcctgtta  360
ctagcactca catggaacaa atggcctcta gcctggaggc ttgctgaagg ctgtatgctg  420
ttctgatcct gaagttcggg ttcgttttgg cctctgactg acgaacccga accaggatca  480
gaacaggaca caaggcctgt tactagcact cacatggaac aaatggcctc tctagaat    538

SEQ ID NO: 10           moltype = DNA   length = 540
FEATURE                 Location/Qualifiers
source                  1..540
                        mol_type = other DNA
                        organism = synthetic construct
SEQUENCE: 10
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgaa atcttccggt ggttccactg cgtttggcc tctgactgac   180
gcagtggaac ccggaagatt tcaggacaca aggcctgtta ctagcactca catggaacaa  240
atggcctcta gcctggaggc ttgctgaagg ctgtatgctg atatcctgaa tatggtatgc  300
agcgttttgg cctctgactg acgctgcata ccattcagga tatcaggaca caaggcctgt  360
tactagcact cacatggaac aaatggcctc tagcctggag gcttgctgaa ggctgtatgc  420
tgtttaaagc tcaaacgcgt tcgccgtttt ggcctctgac tgacggcgaa cgcgtgagct  480
ttaaacagga cacaaggcct gttactagca ctcacatgga acaaatggcc tctctagaat  540

SEQ ID NO: 11           moltype = DNA   length = 540
FEATURE                 Location/Qualifiers
source                  1..540
                        mol_type = other DNA
                        organism = synthetic construct
SEQUENCE: 11
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgta ataaaggtct gggaatcacc cgtttggcc tctgactgac   180
gggtgattcc gacctttatt acaggacaca aggcctgtta ctagcactca catggaacaa  240
atggcctcta gcctggaggc ttgctgaagg ctgtatgctg taatacgcca gatcaccatc  300
agcgttttgg cctctgactg acgctgatgg tgctggcgta ttacaggaca caaggcctgt  360
tactagcact cacatggaac aaatggcctc tagcctggag gcttgctgaa ggctgtatgc  420
tgatacagaa acgaaggttc aggccgtttt ggcctctgac tgacggcctg aacccgtttc  480
tgtatcagga cacaaggcct gttactagca ctcacatgga acaaatggcc tctctagaat  540

SEQ ID NO: 12           moltype = DNA   length = 540
FEATURE                 Location/Qualifiers
source                  1..540
                        mol_type = other DNA
                        organism = synthetic construct
SEQUENCE: 12
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgtc agatcgctgt ggtaaacagg cgtttggcc tctgactgac   180
gcctgtttac cagcgatctg acaggacaca aggcctgtta ctagcactca catggaacaa  240
atggcctcta gcctggaggc ttgctgaagg ctgtatgctg agaatcagat cagatagcga  300
tccgttttgg cctctgactg acggatcgct atctgctgat tctcaggaca caaggcctgt  360
tactagcact cacatggaac aaatggcctc tagcctggag gcttgctgaa ggctgtatgc  420
tgaaacatgc caacagcaga atgccgtttt ggcctctgac tgacggcatt ctgctgggca  480
tgtttcagga cacaaggcct gttactagca ctcacatgga acaaatggcc tctctagaat  540

SEQ ID NO: 13           moltype = DNA   length = 540
FEATURE                 Location/Qualifiers
source                  1..540
                        mol_type = other DNA
                        organism = synthetic construct
SEQUENCE: 13
gccaccatgg ccaccggctc tcgcacaagc ctgctgctgg ctttcggact gctgtgcctg   60
ccttggctcc aggagggctc cgccgctagc atcgataccg tcgctatgtg ctggaggctt  120
gctgaaggct gtatgctgac aatcagatat ggttgctcgg cgtttggcc tctgactgac   180
gccgagcaac tatctgattg tcaggacaca aggcctgtta ctagcactca catggaacaa  240
atggcctcta gcctggaggc ttgctgaagg ctgtatgctg tttcacaatg catcgttcag  300
cgcgttttgg cctctgactg acgcgctgaa cggcattgtg aaacaggaca caaggcctgt  360
tactagcact cacatggaac aaatggcctc tagcctggag gcttgctgaa ggctgtatgc  420
tgacaataat gccaacaggg tggtcgtttt ggcctctgac tgacgaccac cctgggcatt  480
attgtcagga cacaaggcct gttactagca ctcacatgga acaaatggcc tctctagaat  540
```

-continued

```
SEQ ID NO: 14          moltype = DNA   length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt cccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc cttttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa cgctagacggttaat        1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcgga gcattaagcg cggcgggtgt ggtggttacg ccgcagcgtga ccgctacact  1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg ggccatcgcc   1560
ctgatagacg gttttttcgcc ctttgacgtt ggagtccacg ttctttaata gtggactctt   1620
gttccaaact ggaacaacac tcaaccctat ctcggtctat tctttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga aaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
```

```
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg cccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccc aattttgtat ttatttattt tttaattatt ttgtgcagcg atgggggcgg  5160
ggggggggg gggcgcgcgc caggcggggc ggggcggggc gaggggcggg gcggggcgag  5220
gcgggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg ccccgcccgg cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacatttttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctga cttggctcca ggagggctcc  5880
gccgctagca tcgataccgt cgctatgtgc tggaggcttg ctgaaggctg tatgctgatc  5940
aatcggattg cggtaatcgc gtttttggcct ctgactgacg cgattaccga tccgattgat  6000
caggacacaa ggcctgttac tagcactcac atggaacaaa tggcctctag cctggaggct  6060
tgctgaaggc tgtatgctga tctttgctaa attggtgcac gcgtttttggc ctctgactga  6120
cgcgtgcacc attagcaaag atcaggacac aaggcctgtt actagcactc acatggaaca  6180
aatggcctct agcctggagg cttgctgaag gctgtatgct gacttcaatc acaattccag  6240
cgccgttttg gcctctgact gacggcgctg gaagtgattg aagtcaggac acaaggcctg  6300
ttactagcac tcacatggaa caaatggcct ctctagaat                         6339
```

```
SEQ ID NO: 15          moltype = DNA   length = 6339
FEATURE                Location/Qualifiers
source                 1..6339
                       mol_type = other DNA
                       organism = synthetic construct
SEQUENCE: 15
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccctctcct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatt  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta tcattaact acaaggcaat cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg gccatcgcc   1560
ctgatagacg gttttcgccc ctttgacgtt ggagtccacg ttctttaata gtggactctt  1620
gttccaaact ggaacaacac tcaacctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg tgatttgac tgtctccggc ctttctcacc cgtttgaatc tttacctaca  2040
cattactcag gcattgcatt taaaatatat gagggttcta aaaatttttta tccttgcgtt  2100
gaaataaagg cttctcccgc aaaagtatta cagggtcata tgttttttgg tacaaccgat  2160
ttagcttttat gctctgaggc tttattgctt aattttgcta attctttgcc ttgcctgtat  2220
gatttattgg atgttggaat tcctgatgcg gtattttctc cttacgcatc tgtgcggtat  2280
```

-continued

```
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttattttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcatttttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctcacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggcctttttt  4320
acggttcctg gccttttgct ggccttttgc tcacatgttc tttcctgcgt tatccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttgtc gccgggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccc aattttgtat ttatttattt tttaattatt ttgtgcagcg atggggggcgg  5160
ggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggcttca ggagggcctcc  5880
gccgctagca tcgataccgt cgctatgtgc tggaggcttg ctgaaggctg tatgctgtaa  5940
tctttcgctg gctgcagttc gttttggcct ctgactgacg aactcagcg cgaaagatta  6000
caggacacaa ggcctgttac tagcactcac atggaacaaa tggcctctag cctggaggct  6060
tgctgaaggc tgtatgctgt gttaatgctg atgtcacgct gcgttttgac ctctgactga  6120
cgcagcgtga ccagcattaa cacaggacac aaggcctgtt actagcactc acatggaaca  6180
aatggcctct agcctggagg cttgctgaag gctgtatgct gttcacctgg ttaacacata  6240
caccgttttg gcctctgact gacggtgtat gtgaaccagg tgaacaggac acaaggcctg  6300
ttactagcac tcacatggaa caaatggcct ctctagaat                        6339
```

SEQ ID NO: 16        moltype = DNA   length = 6339
FEATURE              Location/Qualifiers
source               1..6339
                     mol_type = other DNA
                     organism = synthetic construct
SEQUENCE: 16

```
aatcaacctc tggattacaa aatttgtgaa agattgactg gtattcttaa ctatgttgct  60
cctttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccccact  240
```

```
ggttggggca ttgccaccac ctgtcagctc ctttccggga cttttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc cttttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggct taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctccctttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccgggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc cttcctcacc cgtttgaatc tttacctaca  2040
cattactcag gcattgcatt taaaatatat gagggttcta aaaatttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcacttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cactttaaa gttctgctat gtggcgcggt attatcccgt attgacgccg gcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
tttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat aatagactgg  3300
atggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg ggggttcgt gcacacagcc cagcttggag cgaacgacct acaccgaact  4080
gagatacta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gcctttttgc ggccttttgc tcacatgttc tttcctgcgt tatccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
```

```
cccagtacat gaccttatgg gactttccta cttggcagta catctacgta ttagtcatcg    5040
ctattaccat ggtcgaggtg agccccacgt tctgcttcac tctccccatc tccccccct     5100
ccccaccccc aattttgtat ttatttattt tttaattatt ttgtgcagcg atggggcgg     5160
gggggggggg gggcgcgcgc caggcgggc ggggcggggc gaggggcggg gcggggcgag      5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgcccgtgc cccgctccgc cgccgcctcg cgccgcccgc cccggctctg     5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacatttag gacgggactt gggtgactct agggcactgg     5640
ttttctttcc agagagcgga acaggcgagg aaaagtagtc ccttctcggc gattctgcgg    5700
agggatctcc gtgggcggt gaacgccgat gatgcctcta ctaaccatgt tcatgttttc     5760
ttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgatt     5940
tcttcctgtg cgctttcgcc gttttggcct ctgactgacg gcgaaagcgc aggaagaaat    6000
caggacacaa ggcctgttac tagcactcac atggaacaaa tggcctctag cctggaggct    6060
tgctgaaggc tgtatgctga gaataatcag atcagcacgc tcgtttggc ctctgactga     6120
cgagcgtgct gctgattatt ctcaggacac aaggcctgtt actagcactc acatggaaca    6180
aatggcctct agcctggagg cttgctgaag gctgtatgct gtaatcaggc tgaattcaga    6240
tagcgttttg gcctctgact gacgctatct gaacagcctg attacaggac acaaggcctg    6300
ttactagcac tcacatggaa caaatggcct ctctagaat                           6339
```

SEQ ID NO: 17          moltype = DNA  length = 6339
FEATURE                Location/Qualifiers
source                 1..6339
                       mol_type = other DNA
                       organism = synthetic construct
SEQUENCE: 17

```
aatcaacctc tggattacaa aatttgtgaa agattgactg gtattcttaa ctatgttgct    60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc     600
gataccgtcg agatctaact tgtttattgc agcttataat ggttacaaat aaagcaatag     660
catcacaaat ttcacaaata aagcatttt ttcactgcat tctagttgtg gtttgtccaa      720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggcg taccgttcct gtctaaaatc cctttaatcg gcctcctgtt tagctccgtc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tcctttctcg ccacgttcgc    1440
cggctttccc cgtcaagctc taaatcgggg gctcccttta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaaccctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaattat cagctagaac ggttgaatat     1980
catattgatg gtgatttgac tgtctccggc ctttctcacc cgtttgaatc tttacctaca    2040
cattactcag gcattgcatt taaaatatat gagggttcta aaaattttta tccttgcgtt    2100
gaaataaagg cttctcccgc aaaagtatta cagggtcata atgtttttgg tacaaccgat    2160
ttagctttat gctctgaggc tttattgctt aattttgcta attctttgcc ttgcctgtat    2220
gatttattgg atgttggaat tcctgatgcg gtattttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctatttttat aggttaatgt    2520
catgataata atggtttctt agacgtcagg tggcactttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
```

-continued

```
actcggtcgc cgcatacact attctcagaa tgacttggtt gagtactcac cagtcacaga   3000
aaagcatctt acggatggca tgacagtaag agaattatgc agtgctgcca taaccatgag   3060
tgataaacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacctta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac tctgacttga gcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagaggggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct    5100
ccccacccc aatttgtat ttatttattt tttaattatt ttgtgcagcg atggggggcgg    5160
gggggggggg gggcgcgcgc caggcggggc ggggcggggc gaggggcggg gcggggcgag   5220
gcggagaggt gcggcgcag ccaatcagag cggcgcgctc cgaaagtttc cttttatggc    5280
gaggcggcag cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
tttctttcc agagagcgga acaggcgagg aaaagtagtc ccttctcggc gattctgcgg    5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgata   5940
atcaccgctg caggttcagc gtttttggcct ctgactgacg ctgaacctgg cggtgattat   6000
caggacacaa ggcctgttac tagcactcac atggaacaaa tggcctctag cctggaggct   6060
tgctgaaggc tgtatgctgt tcaatcgcgt attggtaatc gcgttttggc ctctgactga   6120
cgcgattacc aacgcgattg aacaggacac aaggcctgtt actagcactc acatggaaca   6180
aatggcctct agcctggagg cttgctgaag gctgtatgtc gtgatcatgc tgaaaatggt   6240
gcacgttttg gcctctgact gacgtgcacc attcagcatg atcacaggac acaaggcctg   6300
ttactagcac tcacatggaa caaatggcct ctctagaat                           6339
```

```
SEQ ID NO: 18        moltype = DNA   length = 6339
FEATURE              Location/Qualifiers
source               1..6339
                     mol_type = other DNA
                     organism = synthetic construct
SEQUENCE: 18
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttcgacgt ctttcgcttt ccccctcact   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcggggtta atcattaact acaaggaacc cctagtgatg gagttggcca   840
ctccctctct gcgcgctcgc tcgctcactg aggccggggc accaaaggtc gcccgacgcc   900
```

```
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt aaaaatatat gagggttcta aaaatttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtatttttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtat  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaaagcatct tacggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagaggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccccc aattttgtat ttatttattt ttaattatt ttgtgcagcg atggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcggg gagtcgctgc gacgctgcc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
```

```
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgagg   5940
taatatcctg acgctcagcc gttttggcct ctgactgacg gctgagcgtg gatattacct   6000
caggacacaa ggcctgttac tagcactcac atggaacaaa tggcctctag cctggaggct   6060
tgctgaaggc tgtatgctgt acagaatcag ataatcagcg ccgttttggc ctctgactga   6120
cggcgctgat tctgattctg tacaggacac aaggcctgtt actagcactc acatggaaca   6180
aatggcctct agcctggagg cttgctgaag gctgtatgct gtcatgttta aaaattcgct   6240
gcgcgttttg gcctctggact gacgcgcagc gaatttaaac atgacaggac acaaggcctg   6300
ttactagcac tcacatggaa caaatggcct ctctagaat                          6339
```

SEQ ID NO: 19          moltype = DNA   length = 6339
FEATURE                Location/Qualifiers
source                 1..6339
                       mol_type = other DNA
                       organism = synthetic construct
SEQUENCE: 19

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgc ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta caggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcacttt cggggaaatg tgcgcggaac   2580
ccctatttgt ttatttttct aaatacattc aaatatgtat ccgctcatga cacataaacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
```

-continued

```
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg ggggggttcgt gcacacagcc cagcttggag cgaacgacct acaccgaact  4080
gagatacccta cagcgtgagc tatgagaaag cgccacgctt cccgaaggga gaaaggcgga  4140
caggtatccg gtaagcggca gggtcggaac aggagagcgc acgagggagc ttccagggga  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggcctttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagagc cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tccccccct  5100
ccccacccccc aattttgtat ttatttattt tttaattatt ttgtgcagcg atggggggg  5160
ggggggggg gggcgcgcgc caggcgggc ggggcgggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggctg ctgaaggctg tatgctgatg  5940
aatcgggttg tctgaatcgc gttttggcct ctgactgacg cgattcagaa cccgattcat  6000
caggacacaa ggcctgttac tagcactcac atggaacaaa tggcctctag cctggaggct  6060
tgctgaaggc tgtatgctga acactttgct atatcatcct gcgttttggc ctctgactga  6120
cgcaggatga tagcaaagtg ttcaggacac aaggcctgtt actagcactc acatggaaca  6180
aatggcctct agcctggagg cttgctgaag gctgtatgct gttctgttcg ttaagctaat  6240
gctcgttttg gcctctgact gacgagcatt agcaacgaac agaacaggac acaaggcctg  6300
ttactagcac tcacatggaa caaatggcct ctctagaat              6339
```

SEQ ID NO: 20          moltype = DNA   length = 6339
FEATURE                Location/Qualifiers
source                 1..6339
                       mol_type = other DNA
                       organism = synthetic construct
SEQUENCE: 20

```
aatcaacctc tggattacaa aatttgtgaa agattgactg gtattcttaa ctatgttgct  60
cctttacgc tatgtggata cgctgcttta atgccttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccctcct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcatttt ttcactgcat tctagttgtg gtttgtccaa  720
actcatcaat gtatcttatc atgtctggat ctcgacctcg actagagcat ggctacgtag  780
ataagtagca tggcgggtta atcattaact acaggaacc cctagtgatg gagttggcca  840
ctccctctct gcgcgctcgc tcgctcactg aggccgggc accaaaggtc gcccgacgcg  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctgcgtgtaa tattgttctg gatattacca gcaaggccga tagtttgagt  1080
tcttctactc aggcaagtga tgttattact aatcaaagaa gtattgcgac aacggttaat  1140
ttgcgtgatg acagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
```

-continued

```
ctgatagacg gttttttcgcc cttttgacgtt ggagtccacg ttcttttaata gtggactctt   1620
gttccaaact ggaacaacac tcaacccctat ctcggtctat tcttttttgatt tataagggat  1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt  1800
ggggctttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat  2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttttat aggttaatgt   2520
catgataata atggtttctt agacgtcagg tggcactttt cggggaaatg tgcgcggaac   2580
ccctatttgt ttattttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcatttttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcacg gcctttttgct ggcctttttgc tcacatgttc tttcctgcgt tatccccctg   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
ccccacccccc aatttttgtat ttatttattt tttaattatt ttgtgcagcg atgggggcgg   5160
gggggggggg gggcgcgcgc caggcggggc ggggcggggc gagggcgggg cggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actaccgcg ttactaaaac aggtaagtcc ggcctccgcg ccgggttttg gcgcctcccg   5460
cgggcgcccc cctcctcacg cgcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacatttttag gacgggactt gggtgactct agggcactgg   5640
ttttctttcc agagagcgga acaggcgagg aaaagtagtc ccttctcggc gattctgcgg   5700
agggatctcc gtgggcggt gaacgccgat gatgcctcta ctaaccatgt tcatgttttc   5760
tttttttttttc tacaggtcct gggtgacgaa caggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctggag   5940
cattagcaat gcgaacagaa gtttttggcct ctgactgact tctgttcgtt gctaatgctg   6000
caggacacaa ggcctgttac tagcactcac atggaacaaa tggcctctag cctgaggct   6060
tgctgaaggc tgtatgctga aacataatgg attcagcagc gcgttttggc ctctgactga   6120
cgcgctgctg accattatgt ttcaggcacac aaggcctgtt actagcactc acatggaaca   6180
aatggcctctc agcctggagg cttgctgaag gctgtatgct gttatctttg cgaagctgcc   6240
atccgttttg gcctctgact gacggatggc agccgcaaag ataacaggac acaaggcctg   6300
```

-continued

```
ttactagcac tcacatggaa caaatggcct ctctagaat                                6339

SEQ ID NO: 21          moltype = DNA   length = 6337
FEATURE                Location/Qualifiers
source                 1..6337
                       mol_type = other DNA
                       organism = synthetic construct
SEQUENCE: 21
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggc taccgttcct gtctaaaatc cctttaatcg gcctcctgtt tagctcccgc     1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tcctttctcg ccacgttcgc    1440
cggctttccc cgtcaagctc taaatcgggg ctccctttta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaaccctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcca aaaattttta tccttgcgtt    2100
gaaataaagg cttctcccgc aaaagtatta caggggtcata atgttttttgg tacaaccgat   2160
ttagctttat gctctgaggc tttattgctt aattttgcta attctttgcc ttgcctgtat    2220
gatttattgg atgttggaat cctgatgcg gtattttctc cttacgcatc tgtgcggtat     2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctattttat aggttaatgt     2520
catgataata atggtttctt agacgtcagg tggcactttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt cccttttttg cggcattttg ccttcctgtt tttgctcacc cagaaacgct    2760
ggtgaaagta aaagatgctg aagatcagt gggtgcacga gtgggttaca tcgaactgga     2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
ttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat aatagactg     3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagataccta cagcgtgagc tatgagaaag cgccacgctt cccgaaggga aaaggcgga     4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
```

```
tttgtgatgc tcgtcagggg ggcggagcct atggaaaaac gccagcaacg cggccttttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc ggctcgctc gctcactgag    4560
gccgccgggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tcccccccct    5100
ccccaccccc aattttgtat ttatttattt tttaattatt ttgtgcagcg atggggggcgg    5160
gggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aacccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtgggtcggt gaacgccgat gatgcctcta ctaaccatgt tcatgttttc    5760
ttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctggct    5940
cctccacttg gtggtttggt tttggcctct gactgacgcg gcaacattct ggtgattaca    6000
ggacacaagg cctgttacta gcactcacat ggaacaaatg gcctctagcc tggaggcttg    6060
ctgaaggctg tatgctgtca taatcgctat ttggtgcggc gttttggcct ctgactgacg    6120
ccgcaccaaa gcgattatga caggacacaa ggcctgttac tagcactcac atggaacaaa    6180
tggcctctag cctggaggct tgctgaaggc tgtatgctgt tctgatcctg aagttcgggt    6240
tcgtttggc ctctgactga cgaacccgaa ccaggatcag aacaggacac aaggcctgtt    6300
actagcactc acatggaaca aatggcctct ctagaat    6337
```

```
SEQ ID NO: 22          moltype = DNA   length = 6339
FEATURE                Location/Qualifiers
source                 1..6339
                       mol_type = other DNA
                       organism = synthetic construct
SEQUENCE: 22
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg atagagcat ggctacgtag    780
ataagtagca tggcgggtta tcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggc taccgttcct gtctaaaatc cctttaatcg gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tcctttctcg ccacgttcgc    1440
cggctttccc cgtcaagctc taaatcgggg ctccctttag ggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaacctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaatttta tccttgcgtt    2100
gaaataaagg cttctcccgc aaaagtatta cagggtcata tgtttttgg tacaaccgat    2160
ttagctttat gctctgaggc tttattgctt aattttgcta attctttgcc ttgcctgtat    2220
```

-continued

```
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctcc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacgtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccc aattttgtat ttatttattt tttaattatt ttgtgcagcg atggggggcgg  5160
gggggggggg gggcgcgcgc caggcggggc ggggcggggc gaggggcggg gcggggcgag  5220
gcggaggt gcggcggcag ccaatcagag cggcggctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgaaa  5940
tcttccggtg gttccactgc gttttggcct ctgactgacg cagtggaacc cggaagattt  6000
caggacacaa ggcctgttac tagcactcac atggaacaaa tggcctctag cctgtctcag  6060
tgctgaaggc tgtatgctga tatcctgaat atggtatgca gcgtttttggc ctctgactga  6120
cgctgcatac cattcaggat atcaggacac aaggcctgtt actagcactc acatggaaca  6180
aatggcctct agcctggagg cttgctgaag gctgtatgct gtttaaagct caaacgcgtt  6240
cgccgttttg gcctctgact gacggcgaac gcgtgagctt taaacaggac acaaggcctg  6300
ttactagcac tcacatggaa caaatggcct ctctagaat                       6339
```

SEQ ID NO: 23          moltype = DNA   length = 6339
FEATURE                Location/Qualifiers
source                 1..6339
                       mol_type = other DNA
                       organism = synthetic construct
SEQUENCE: 23

```
aatcaacctc tggattacaa aatttgtgaa agattgactg gtattcttaa ctatgttgct  60
cctttacgta tatgtggata cgctgcttta atgcctttgt atcatgctat tgcttcccgt  120
atggctttca ttttctcctc cttgtataaa tcctggttgc tgtctcttta tgaggagttg  180
```

-continued

```
tggcccgttg tcaggcaacg tggcgtggtg tgcactgtgt ttgctgacgc aacccccact   240
ggttggggca ttgccaccac ctgtcagctc ctttccggga ctttcgcttt cccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacgttaat    1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaacccat ctcggtctat tcttttgatt tataagggat    1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt aaaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcacttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aagatcaaa ggatcttctt gagatccttt    3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacctca cagcgtgagc tatgagaaag cgccacgctt cccgaaggga aaaggcgga    4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctg gcgctcgctc gctcactgag    4560
gccgcccggg caaagccggg cgtcggggcg acctttggtc cgcccgccgtc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgaccccc   4800
gcccattgac gtcaataatg acgtatgttc ccatagtaac gccaatagg actttccatt    4860
gacgtcaatg ggtggagtat ttacggtaaa ctgcccactt ggcagtacat caagtgtatc   4920
```

-continued

```
atatgccaag  tacgcccct  attgacgtca  atgacggtaa  atggcccgcc  tggcattatg  4980
cccagtacat  gaccttatgg  gactttccta  cttggcagta  catctacgta  ttagtcatcg  5040
ctattaccat  ggtcgaggtg  agccccacgt  tctgcttcac  tctccccatc  tccccccct   5100
ccccaccccc  aattttgtat  ttatttattt  tttaattatt  ttgtgcagcg  atgggggcgg  5160
gggggggggg  gggcgcgcgc  caggcggggc  ggggcggggc  gaggggcggg  gcggggcgag  5220
gcggagaggt  gcggcggcag  ccaatcagag  cggcgcgctc  cgaaagtttc  cttttatggc  5280
gaggcggcgg  cggcggcggc  cctataaaaa  gcgaagcgcg  cggcgggcgg  gagtcgctgc  5340
gcgctgcctt  cgcccgtgc   cccgctccgc  cgccgcctcg  cgccgcccgc  cccggctctg  5400
actgaccgcg  ttactaaaac  aggtaagtcc  ggcctccgcg  ccgggttttg  gcgcctcccg  5460
cgggcgcccc  cctcctcacg  gcgagcgctg  ccacgtcaga  cgaagggcgc  agcgagcgtc  5520
ctgatccttc  cgcccggacg  ctcaggacag  cggcccgctg  ctcataagac  tcggccttag  5580
aaccccagta  tcagcagaag  gacattttag  gacgggactt  gggtgactct  agggcactgg  5640
ttttctttcc  agagagcgga  acaggcgagg  aaaagtagtc  ccttctcggc  gattctgcgg  5700
agggatctcc  gtggggcggt  gaacgccgat  gatgcctcta  ctaaccatgt  tcatgtttc   5760
ttttttttc   tacaggtcct  gggtgacgaa  cagggtaccg  ccaccatggc  caccggctct  5820
cgcacaagcc  tgctgctggc  tttcggactg  ctgtgcctgc  cttggctcca  ggagggctcc  5880
gccgctagca  tcgataccgt  cgctatgtgc  tggaggcttg  ctgaaggctg  tatgctgtaa  5940
taaaggtctg  ggaatcaccc  gttttggcct  ctgactgacg  ggtgattccg  acctttatta  6000
caggacacaa  ggcctgttac  tagcactcac  atggaacaaa  tggcctctag  cctggaggct  6060
tgctgaaggc  tgtatgctgt  aatacgccag  atcaccatca  gcgttttggc  ctctgactga  6120
cgctgatggt  gctggcgtat  tacaggacac  aaggcctgtt  actagcactc  acatggaaca  6180
aatggcctct  agcctggagg  cttgctgaag  gctgtatgct  gatacagaaa  cgaaggttca  6240
ggccgttttg  gcctctgact  gacggcctga  acccgtttct  gtatcaggac  acaaggcctg  6300
ttactagcac  tcacatggaa  caaatggcct  ctctagaat              6339

SEQ ID NO: 24        moltype = DNA   length = 6339
FEATURE              Location/Qualifiers
source               1..6339
                     mol_type = other DNA
                     organism = synthetic construct
SEQUENCE: 24
aatcaacctc  tggattacaa  aatttgtgaa  agattgactg  gtattcttaa  ctatgttgct  60
ccttttacgc  tatgtggata  cgctgcttta  atgcctttgt  atcatgctat  tgcttcccgt  120
atggctttca  ttttctcctc  cttgtataaa  tcctggttgc  tgtctctttga  tgaggagttg  180
tggcccgttg  tcaggcaacg  tggcgtggtg  tgcactgtgt  ttgctgacgc  aacccccact  240
ggttggggca  ttgccaccac  ctgtcagctc  ctttccggga  ctttcgcttt  ccccctccct  300
attgccacgg  cggaactcat  cgccgcctgc  cttgcccgct  gctggacagg  ggctcggctg  360
ttgggcactg  acaattccgt  ggtgttgtcg  gggaaatcat  cgtcctttcc  ttggctgctc  420
gcctgtgttg  ccacctggat  tctgcgcggg  acgtccttct  gctacgtccc  ttcggccctc  480
aatccagcgg  accttccttc  ccgcggcctg  ctgccggctc  tgcggcctct  tccgcgtctt  540
cgccttcgcc  ctcagacgag  tcggatctcc  ctttgggccg  cctccccgcc  taagcttatc  600
gataccgtcg  agatctaact  tgtttattgc  agcttataat  ggttacaaat  aaagcaatag  660
catcacaaat  ttcacaaata  aagcattttt  ttcactgcat  tctagttgtg  gtttgtccaa  720
actcatcaat  gtatcttatc  atgtctggat  ctcgacctcg  actagagcat  ggctacgtag  780
ataagtagca  tggcgggtta  atcattaact  acaaggaacc  cctagtgatg  gagttggcca  840
ctccctctct  gcgcgctcgc  tcgctcactg  aggccgggcg  accaaaggtc  gcccgacgcc  900
cgggctttgc  ccgggcggcc  tcagtgagcg  agcgagcgcg  cagctggcgt  aatagcgaag  960
aggcccgcac  cgatcgccct  tcccaacagt  tgcgcagcct  gaatggcgaa  tggcgattcc  1020
gttgcaatgg  ctggcggtaa  tattgttctg  gatattacca  gcaaggccga  tagtttgagt  1080
tcttctactc  aggcaagtga  tgttattact  aatcaaagaa  gtattgcgac  aacggttaat  1140
ttgcgtgatg  gacagactct  tttactcggt  ggcctcactg  attataaaaa  cacttctcag  1200
gattctggcg  taccgttcct  gtctaaaatc  cctttaatcg  gcctcctgtt  tagctcccgc  1260
tctgattcta  acgaggaaag  cacgttatac  gtgctcgtca  aagcaaccat  agtacgcgcc  1320
ctgtagcggc  gcattaagcg  cggcgggtgt  ggtggttacg  cgcagcgtga  ccgctacact  1380
tgccagcgcc  ctagcgcccg  ctcctttcgc  tttcttccct  tcctttctcg  ccacgttcgc  1440
cggctttccc  cgtcaagctc  taaatcgggg  gctcccttta  gggttccgat  ttagtgcttt  1500
acggcacctc  gaccccaaaa  aacttgatta  gggtgatggt  tcacgtagtg  ggccatcgcc  1560
ctgatagacg  gtttttcgcc  ctttgacgtt  ggagtccacg  ttctttaata  gtggactctt  1620
gttccaaact  ggaacaacac  tcaaccctat  ctcggtctat  tcttttgatt  tataagggat  1680
tttgccgatt  tcggcctatt  ggttaaaaaa  tgagctgatt  taacaaaaat  ttaacgcgaa  1740
ttttaacaaa  atattaacgt  ttacaattta  aatatttgct  tatacaatct  tcctgttttt  1800
ggggcttttc  tgattatcaa  ccggggtaca  tatgattgac  atgctagttt  tacgattacc  1860
gttcatcgat  tctcttgttt  gctccagact  ctcaggcaat  gacctgatag  cctttgtaga  1920
gacctctcaa  aaatagctac  cctctccggc  atgaatttat  cagctagaac  ggttgaatat  1980
catattgatg  gtgatttgac  tgtctccggc  ctttctcacc  cgtttgaatc  tttacctaca  2040
cattactcag  gcattgcatt  taaaatatat  gagggttcta  aaaatttttta  tccttgcgtt  2100
gaaataaagg  cttctcccgc  aaaagtatta  cagggtcata  atgtttttgg  tacaaccgat  2160
ttagctttat  gctctgaggc  tttattgctt  aattttgcta  attctttgcc  ttgcctgtat  2220
gatttattgg  atgttggaat  tcctgatgcg  gtattttctc  cttacgcatc  tgtgcggtat  2280
ttcacaccgc  atatggtgca  ctctcagtac  aatctgctct  gatgccgcat  agttaagcca  2340
gccccgacac  ccgccaacac  ccgctgacgc  gccctgacgg  gcttgtctgc  tcccggcatc  2400
cgcttacaga  caagctgtga  ccgtctccgg  gagctgcatg  tgtcagaggt  tttcaccgtc  2460
atcaccgaaa  cgcgcgagac  gaaagggcct  cgtgatacgc  ctatttttat  aggttaatgt  2520
catgataata  atggtttctt  agacgtcagg  tggcacttt   cggggaaatg  tgcgcggaac  2580
ccctatttgt  ttatttttct  aaatacattc  aaatatgtat  ccgctcatga  gacaataacc  2640
ctgataaatg  cttcaataat  attgaaaaag  gaagagtatg  agtattcaac  atttccgtgt  2700
cgcccttatt  cccttttttg  cggcattttg  ccttcctgtt  tttgctcacc  cagaaacgct  2760
ggtgaaagta  aaagatgctg  aagatcagtt  gggtgcacga  gtgggttaca  tcgaactgga  2820
tctcaacagc  ggtaagatcc  ttgagagttt  tcgccccgaa  gaacgttttc  caatgatgag  2880
```

```
cactttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccagggga   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtag   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
ggggggggg gggcgcgcgc caggcggggc ggggcggggc gaggggcggg gcggggcgca   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ggggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacatttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtca   5940
gatcgctgtg gtaaacaggc gttttggcct ctgactgacg cctgtttacc agcgatctga   6000
caggacacaa ggcctgttac tagcactcac atggaacaaa tggcctctag cctgagggct   6060
tgctgaaggc tgtatgctga gaatcagatc agatagcgat ccgttttggc ctctgactga   6120
cggatcgcta tctgctgatt ctcaggacac aaggcctgtt actagcactc acatggaaca   6180
aatggcctct agcctggagg cttgctgaag gctgtatgct gaaacatgcc aacagcagaa   6240
tgccgttttg gcctctgact gacggcattc tgctgggcat gtttcaggac acaaggcctg   6300
ttactagcac tcacatggaa caaatggcct ctctagaat                            6339
```

```
SEQ ID NO: 25         moltype = DNA   length = 6339
FEATURE               Location/Qualifiers
source                1..6339
                      mol_type = other DNA
                      organism = synthetic construct
SEQUENCE: 25
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg atctaact tgtttattgc agcttataat ggttacaaat aaagcaatag   660
catcacaaat ttcacaaata aagcattttt ttcactgcat tctagttgtg tttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
```

-continued

```
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag ccttttgtaga  1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtatttctc cttacgcatc tgtgcggtat    2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt    2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cactttaaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgga   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg ggggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttttt  4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aattttgtat ttatttattt tttaattatt ttgtgcagcg atggggggcgg   5160
ggggggggg gggcgcgcgc caggcggggc ggggcggggc gagggcggg gcggggcgag     5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc    5520
ctgatccttc cgcccggacg ctcaggacag cggcccgctg ctcataagac tcggccttag   5580
```

```
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgaca  5940
atcagatatg gttgctcggc gttttggcct ctgactgacg ccgagcaact atctgattgt  6000
caggacacaa ggcctgttac tagcactcac atggaacaaa tggcctctag cctggaggct  6060
tgctgaaggc tgtatgctgt ttcacaatgc atcgttcagc gcgttttggc ctctgactga  6120
cgcgctgaac ggcattgtga aacaggacac aaggcctgtt actagcactc acatggaaca  6180
aatggcctct agcctggagg cttgctgaag gctgtatgct gacaataatg ccaacagggt  6240
ggtcgttttg gcctctgact gacgaccacc ctgggcatta ttgtcaggac acaaggcctg  6300
ttactagcac tcacatggaa caaatggcct ctctagaat                          6339
```